United States Patent [19]
Kriesel et al.

[11] Patent Number: 6,007,518
[45] Date of Patent: *Dec. 28, 1999

[54] FLUID DELIVERY DEVICE WITH CONFORMABLE ULLAGE AND FILL ASSEMBLY

[75] Inventors: Marshall S. Kriesel, St. Paul; Farhad Kazemzadeh, Bloomington; Matthew B Kriesel, St. Paul, all of Minn.; William W Feng, Lafayette, Calif.

[73] Assignee: Science Incorporated, Bloomington, Minn.

[*] Notice: This patent is subject to a terminal disclaimer.

[21] Appl. No.: 09/149,387

[22] Filed: Sep. 8, 1998

Related U.S. Application Data

[63] Continuation of application No. 08/577,779, Dec. 22, 1995, Pat. No. 5,807,335.

[51] Int. Cl.[6] .................................................. A61M 37/00
[52] U.S. Cl. .............................................. 604/131; 604/132
[58] Field of Search ................................. 604/132, 131, 604/133; 128/DIG. 12

[56] References Cited

U.S. PATENT DOCUMENTS

| | | | |
|---|---|---|---|
| 5,085,656 | 2/1992 | Polaschegg | 604/132 |
| 5,090,963 | 2/1992 | Gross et al. | 604/132 |
| 5,122,116 | 6/1992 | Kriesel et al. | 604/132 |
| 5,205,820 | 4/1993 | Kriesel | 604/132 |
| 5,279,558 | 1/1994 | Kriesel | 604/132 |
| 5,492,533 | 2/1996 | Kriesel | 604/132 |
| 5,545,139 | 8/1996 | Kriesel | 604/132 |
| 5,649,910 | 7/1997 | Kriesel et al. | 604/153 |
| 5,656,032 | 8/1997 | Kriesel et al. | 604/132 |
| 5,693,018 | 12/1997 | Kriesel et al. | 604/132 |
| 5,693,019 | 12/1997 | Kriesel | 604/132 |
| 5,720,729 | 2/1998 | Kriesel | 604/132 |
| 5,735,818 | 4/1998 | Kriesel et al. | 604/132 |
| 5,741,242 | 4/1998 | Kriesel | 604/132 |
| 5,776,103 | 7/1998 | Kriesel et al. | 604/132 |
| 5,779,676 | 7/1998 | Kriesel et al. | 604/132 |
| 5,807,335 | 9/1998 | Kriesel et al. | 604/131 |

*Primary Examiner*—Paul J. Hirsch
*Attorney, Agent, or Firm*—James E. Brunton, Esq

[57] ABSTRACT

A fluid delivery apparatus which embodies a stored energy source such as distendable elastomeric membrane which cooperates with a base and a conformable ullage to define a fluid reservoir and one which includes a unique fill assembly for use in controllably filling the fluid reservoir. The novel fill assembly of the invention enables the fluid reservoir of the fluid delivery portion of the apparatus to be aseptically filled in the field with a wide variety of selected medicinal fluids.

15 Claims, 5 Drawing Sheets

FLUID DELIVERY DEVICE WITH CONFORMABLE ULLAGE AND FILL ASSEMBLY

This is a Continuation of application, U.S. Ser. No. 08/577,779 filed Dec. 22, 1995 now U.S. Pat. No. 5,807,335.

BACKGROUND OF THE INVENTION

1. Field of the Invention

The present invention relates generally to fluid delivery devices for infusion of beneficial agents into a patient. More particularly, the invention concerns a fluid delivery apparatus which includes a conformable ullage and a novel fill assembly for filling the fluid reservoir of the apparatus in the field.

2. Discussion of the Invention

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by medicating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished by gravity flow methods, which typically involve the use of intravenous administration sets and the familiar bottle suspended above the patient. such methods are cumbersome, imprecise and require bed confinement of the patient. Periodic monitoring of the apparatus by the nurse or doctor is required to detect malfunctions of the infusion apparatus.

One of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly. The ullage in these devices, that is the amount of the fluid reservoir or chamber that is not filled by fluid, is provided in the form of a semi-rigid structure having flow channels leading from the top of the structure through the base to inlet or outlet ports of the device. Since the inventions described herein represent improvements over those described in U.S. Pat. No. 5,205,820 this patent is hereby incorporated by reference as though fully set forth herein.

In the semi-rigid ullage configuration described in U.S. Pat. No. 5,205,820, wherein the ullage means is more fully described, the stored energy means of the device must be superimposed over the ullage to form the fluid-containing portion of the reservoir from which fluids are expelled at a controlled rate by the elastomeric membrane of the stored energy means tending to return to a less distended configuration in the direction toward the ullage. With these constructions, the stored energy membrane is typically used at higher extensions over a significantly large portion of the pressure-deformation curve.

For good performance, the elastomeric membrane materials selected for construction of the stored energy membrane must have good memory characteristics under conditions of high extension; good resistance to chemical and radiological degradation; and appropriate gas permeation characteristics depending upon the end application to be made of the device. Once an elastomeric membrane material is chosen that will optimally meet the desired performance requirements, there still remain certain limitations to the level of refinement of the delivery tolerances that can be achieved using the semi-rigid ullage configuration. These result primarily from the inability of the semi-rigid ullage to conform to the shape of the elastomeric membrane near the end of the delivery period. This nonconformity can lead to extended delivery rate tail-off and higher residual problems when extremely accurate delivery is required. For example, when larger volumes of fluid are to be delivered, the tail-off volume represents a smaller portion of the fluid amount delivered and therefore exhibits much less effect on the total fluid delivery profile, but in very small doses, the tail-off volume becomes a larger portion of the total volume. This sometimes places severe physical limits on the range of delivery profiles that may easily be accommodated using the semi-rigid ullage configuration.

As will be better appreciated from the discussion which follows, the apparatus of the present invention provides a unique, disposable fluid dispenser of simple but highly reliable construction that may be adapted to a wide variety of end use applications. A particularly important aspect of the improved apparatus is the incorporation of conformable ullages made of yieldable materials which uniquely conform to the shape of the stored energy membrane as the membrane distends and then returns to a less distended configuration. This novel construction, which permits the overall height of the device to be minimized, will satisfy even the most stringent delivery tolerance requirements and uniquely overcomes the limitation of materials selection. Further a plurality of subreservoirs can be associated with a single ullage thereby making it possible to incorporate a wide variety of delivery profiles within a single device.

The thrust of the present invention is to provide a novel fluid delivery apparatus that includes a conformable ullage of the character described in the preceding paragraph and also includes a unique fill assembly that can be used to controllably fill the fluid reservoir of the apparatus in the field. As will be better understood from the description which follows, the fill assembly of the present invention includes a fluid containing vial subassembly mounted within a unique adapter subassembly that functions to conveniently mate the vial subassembly with the conformable ullage type fluid delivery assembly.

In use, the adapter subassembly of the invention securely interconnects the fluid containing vial with the fluid delivery assembly so that the reservoir of the device can be controllably filled with the fluid contained within the vial assembly. After the reservoir is thus filled, the stored energy means of the fluid delivery device will cooperate with the conformable ullage to controllably expel the fluid from the device.

SUMMARY OF THE INVENTION

It is an object of the present invention to provide a fluid delivery apparatus which embodies a stored energy source such as distendable elastomeric membrane which cooperates with a base and a conformable ullage to define a fluid reservoir and one which includes a unique fill assembly for use in controllably filling the fluid reservoir. The novel fill assembly of the invention enables the fluid reservoir of the fluid delivery portion of the apparatus to be aseptically filled in the field with a wide variety of selected medicinal fluids.

Another object of the present invention is to provide an apparatus of the aforementioned character in which the fill assembly comprises a vial assembly of generally conventional construction that can be prefilled with a wide variety of medicinal fluids.

Another object of the present invention is to provide a fill assembly of the type described in the preceding paragraph in which the prefilled vial subassembly is partially received within a novel adapter subassembly that functions to operably couple the vial subassembly with the fluid delivery portion of the apparatus.

Another object of the invention is to provide viewing means for viewing the amount of fluid remaining within the prefilled vial as the fluid reservoir is being filled.

Another object of the invention is to provide an adapter subassembly of the type described in which the body of the prefilled vial is surrounded by a protective covering to maintain the vial in an aseptic condition until immediately prior to mating the subassembly with the fluid delivery portion of the apparatus.

Another object of the invention is to provide an apparatus as described in the preceding paragraphs in which the adapter subassembly includes locking means for locking the subassembly to the fluid delivery portion of the apparatus following filling of the fluid reservoir thereof.

Another object of the invention is to provide a novel fill assembly which is easy to use, is inexpensive to manufacture, and one which maintains the prefilled vial in aseptic condition until time of use.

Another object of the invention is to provide an apparatus of the character described in the preceding paragraphs which embodies a soft, pliable, conformable mass which defines an ullage within the reservoir of the device which will closely conform to the shape of the stored energy membrane geometry thereby providing a more linear delivery and effectively avoiding extended flow delivery rate tail-off with minimum residual fluid remaining in the reservoir at end of the fluid delivery period.

Another object of the invention is to provide an apparatus of the character described which includes novel fluid rate control means for precisely controlling the rate of fluid flow from the device.

Another object of the invention is to provide an apparatus which, due to its unique construction, can be manufactured inexpensively in large volume by automated machinery.

Other objects of the invention are set forth in U.S. Pat. No. 5,205,820 which is incorporated herein by reference and still further objects will become apparent from the discussion which follows.

DESCRIPTION OF THE INVENTION

Figure 1:
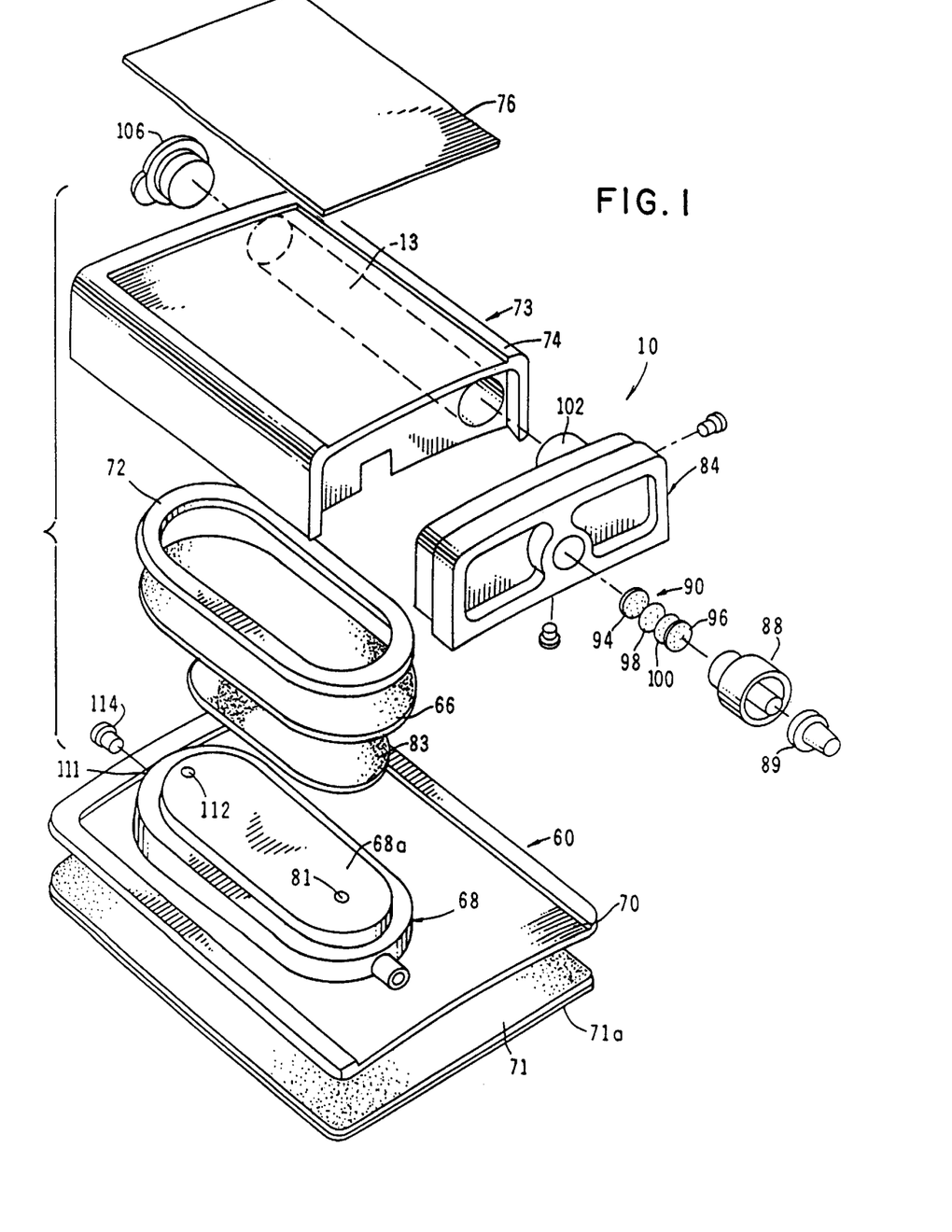
FIG. 1 is a generally perspective, exploded view of one form of the fluid delivery portion of the apparatus of the invention with which the adapter assembly of the invention can be operably interconnected.
Figures 7, 9, 10:
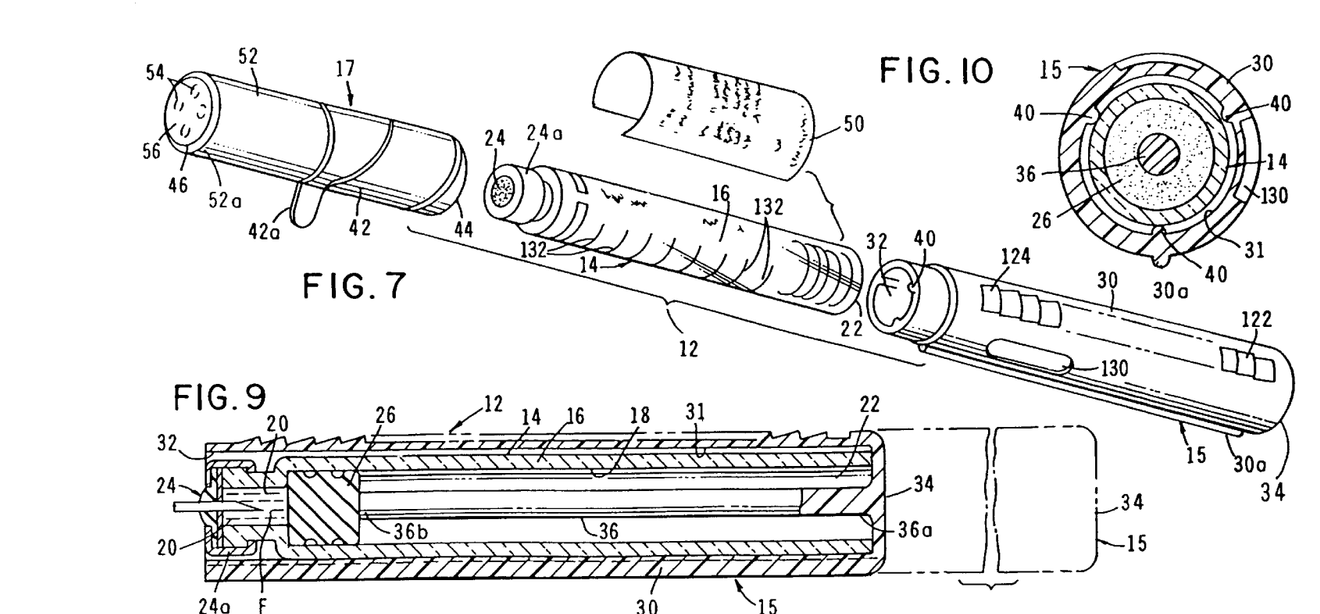
FIG. 7 is a generally perspective view of one form of the adapter assembly of the present invention.
FIG. 9 is a cross-sectional view similar to FIG. 8, but showing the appearance of the component parts of the invention after the plunger of the container has been telescopically moved from a first to a second position.
FIG. 10 is a cross-sectional view taken along lines 10—10 of FIG. 8.

Referring to the drawings and particularly to FIGS. 1 and 7, it is be observed that the apparatus of the invention comprises two major cooperating assemblies, namely the fluid delivery assembly 10 shown in FIG. 1 and the fill assembly 12 shown in FIG. 7. The fluid delivery assembly is similar in many respects to those disclosed in U.S. Pat. No. 5,205,820 in that it includes a base, a stored energy means which cooperates with the base to form a fluid reservoir and a cover assembly which overlays the base and encloses the stored energy means. However, unlike the fluid delivery apparatus disclosed in U.S. Pat. No. 5,205,820, which embodies semi-rigid ullages, the fluid delivery assembly of the present invention includes a novel conformable ullage, the character of which will presently be described. Also, unlike the fluid delivery devices shown in U.S. Pat. No. 5,205,820, the fluid delivery assembly of the present invention includes a uniquely configured receiving chamber 13 which is formed in the cover assembly (FIG. 1) and, in a manner presently to be described, telescopically receives a portion of the novel fill assembly of the invention.

Figure 8:
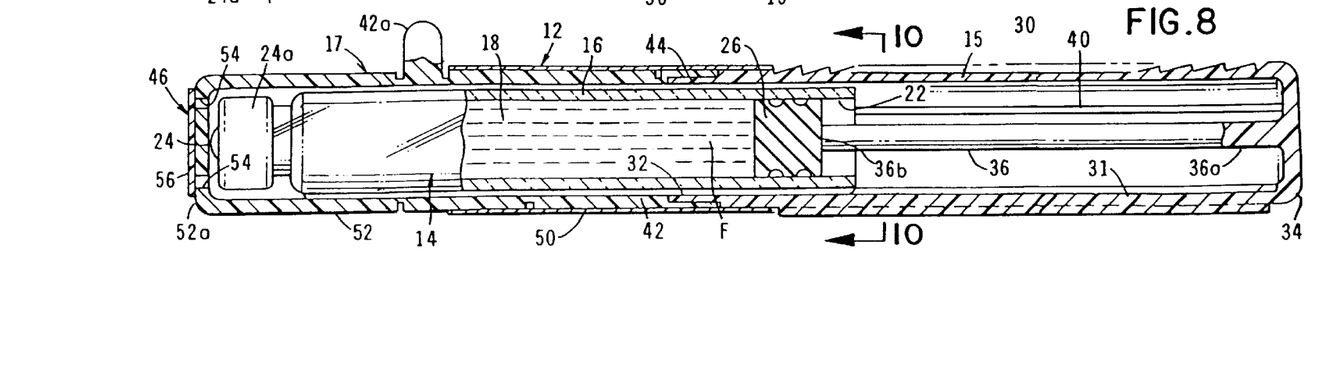
FIG. 8 is an enlarged, cross-sectional view of the adapter assembly illustrated in FIG. 7 as it appears in an assembled configuration.

Turning particularly to FIGS. 7 through 10, one form of the novel fill assembly portion of the apparatus is there shown and generally designated by the numeral 12. This form of the fill assembly comprises a container subassembly 14, an adapter assembly 15, and a cover assembly 17, the character of which will presently be described. Container subassembly 14 includes a body portion 16, having a fluid chamber 18 for containing an injectable fluid "F" provided with first and second open ends 20 and 22 (FIGS. 8 and 9). First open end 20 is sealably closed by closure means here provided in the form of a pierceable septum assembly 24. Septum assembly 24 is held securely in position by a clamping ring 24a. As best seen in FIGS. 8 and 9, a plunger 26 is telescopically movable within chamber 18 of container subassembly 14 from a first location shown in FIG. 8 where it is proximate first open end 22 to a second position shown in FIG. 9 where it is proximate first open end 20. The vial portion of the container subassembly 14 can be constructed of various materials such as glass and plastic.

Referring particularly to FIG. 7, it can be seen that the adapter subassembly 15 comprises a hollow housing 30 having a first open end 32 and a second closed end 34 (FIG. 9). Container subassembly 14 is telescopically receivable within open end 32 of housing 30 in the manner shown in FIG. 8 so that the housing can be moved from the first extended position shown in FIG. 8 to the second vial encapsulation position shown in FIG. 9. Forming an important part of the adapter subassembly is pusher means shown here as an elongated pusher rod 36 which functions to move plunger 26 within fluid chamber 18 from the first position shown in FIG. 8 to the second position shown in FIG. 9. In the form of the invention shown in the drawings, pusher rod 36 has a first end 36a interconnected with closure wall 34 and an opposite end 36b which engages plunger 26 and causes telescopic movement of the plunger within chamber 18 of container subassembly 14 as housing 30 is moved from the extended position into the vial encapsulating position shown in FIG. 9.

As best seen by referring to FIG. 10, the interior wall 31 of housing 30 is provided with circumferentially spaced-apart protuberances 40 which engage and center container subassembly 14 within housing 30. Due to the small surface area presented by protuberances 40, there is little frictional resistance to the sliding movement of container subassembly 14 relative to housing 30 as the housing is moved from the extended position shown in FIG. 8 into the vial encapsulating position shown in FIG. 9.

Cover subassembly 17 of the fill assembly of the present form of the invention includes a spiral wound, frangible portion 42 having a first open end 44 for telescopically receiving body portion 16 of container subassembly 14 (FIG. 8) and a second closed end 46. Portion 42 initially circumscribes a major portion of container subassembly 14 in the manner best seen in FIG. 8. An integral pull tab 42a is provided to permit the spiral wound, frangible portion to be pulled from container subassembly 14 so as to expose a substantial portion of body 16. As best seen in FIG. 7, a medicament label 50 circumscribes spiral wound portion 42 and serves to prevent accidental unwinding of the spiral portion from the container subassembly 14. However, upon pulling tab 42a, the spiral portion will unwind and, in so doing, will tear medicament label 50 so that the spiral portion 42 of the covering as well as a cylindrical portion 52 which, also comprises a part of the cover assembly, can be slipped from the container 14 so as to expose to view septum assembly 24.

As shown in FIGS. 7 and 8, the apertured end 52a of cylindrical portion 52 of subassembly 17 is provided with venting apertures 54 which are covered by a porous vent patch 56 which can be constructed from any suitable porous material that will permit air entrapped within the interior of cover subassembly 17 to be expelled to atmosphere as the subassembly is placed over container subassembly 14.

Figure 2:
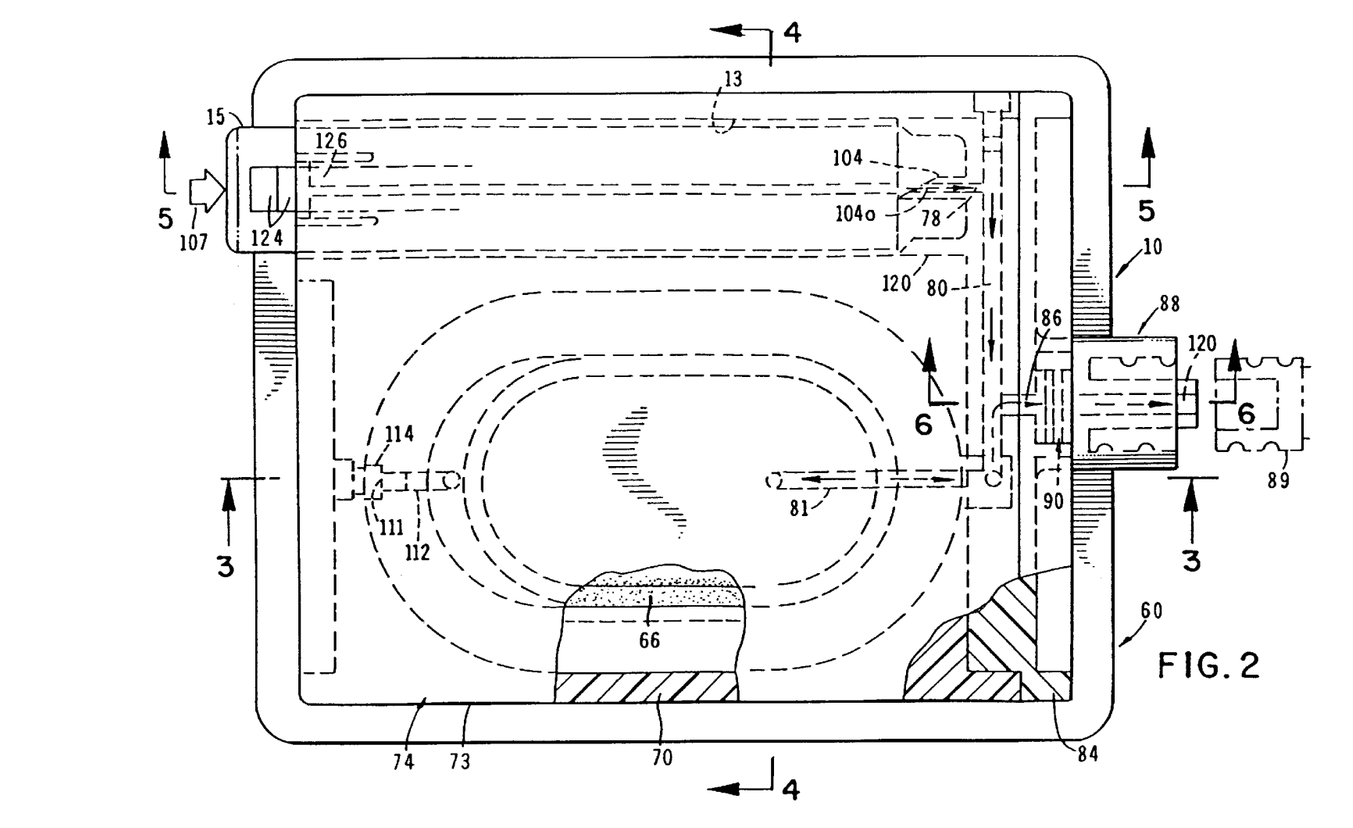
FIG. 2 is a plan view of the fluid delivery portion shown in FIG. 1, partly broken away to show internal construction and shown coupled with the fill assembly of the apparatus.
Figure 3:
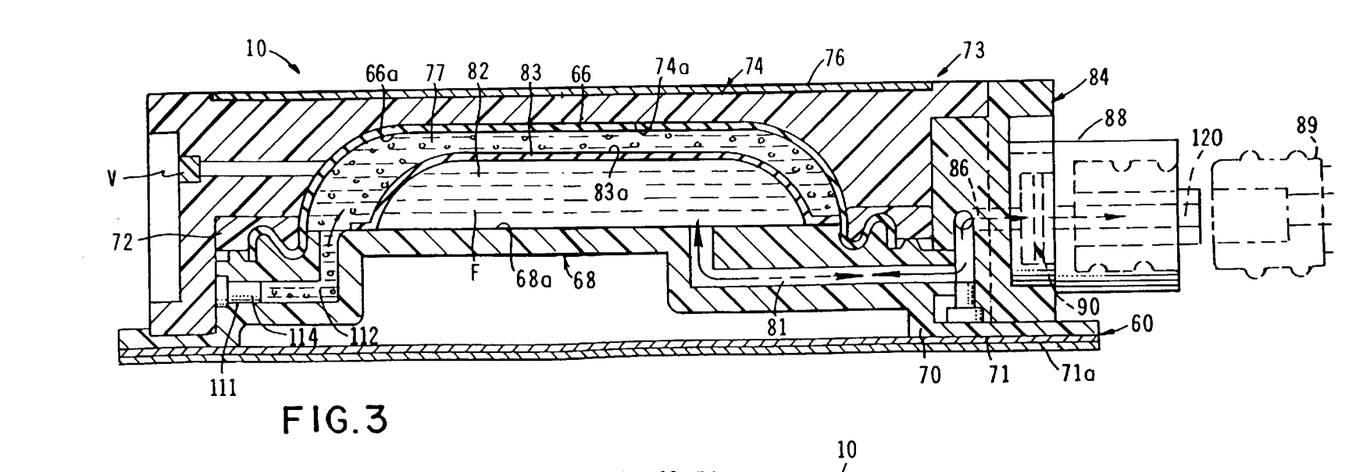
FIG. 3 is a cross-sectional view taken along lines 3—3 of FIG. 2.
Figure 4:
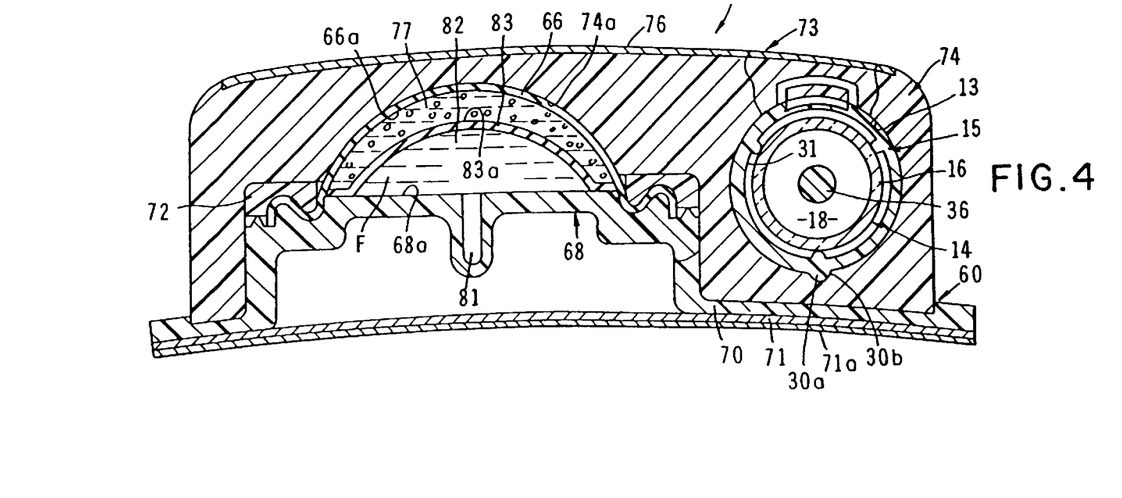
FIG. 4 is a cross-sectional view taken along lines 4—4 of FIG. 2.

Turning once again to FIGS. 1 through 6, the fluid delivery assembly portion 10 of the apparatus can be seen to include a base subassembly 60, a cover subassembly 74 receivable over base subassembly 60, and a stored energy means, here provided in the form of a distendable membrane 66 (FIGS. 3 and 4). As best seen in FIGS. 3 and 4 the periphery of membrane 66 is sealably connected to an upraised portion 68 formed on base member 70. Base member 70 forms a part of base assembly 60 as does a clamping ring 72 which functions to clamp membrane 66 to upraised portion 68 (FIG. 1). Affixed to member 70 is a thin, planar shaped foam pad 71 having an adhesive coating provided on both its upper and lower surfaces. The adhesive coating on the upper surface of the pad enables the pad to be affixed to the lower surface of base member 70. As indicated in FIGS. 3 and 4, a peel strip 71a is connected to the bottom surface of foam pad 71 by the adhesive coating provided thereon. when the device is to be used, peel strip 71a can be stripped away from the pad so that the adhesive on the lower surface thereof can be used to releasably affix the apparatus of the invention to the patient's body.

Turning particularly to FIGS. 1 and 3, it can be seen that the cover subassembly 73 includes a cover member 74 and a medicament label 76. Cover member 73 is provided with the previously identified elongated receiving chamber 13 which is adapted to receive a portion of the fill subassembly of the invention. In a manner presently to be described the fluid container portion of the fill subassembly communicates via passageways 78, 80 and 81 with a fluid reservoir 82 which is uniquely formed between a deformable barrier member 83 and the upper surface 68a of upraised portion 68 of base member 70 (FIGS. 3 and 4). Disposed between barrier member 83 and distendable membrane 66 is the important conformable ullage means of the invention, the unique nature of which will presently be discussed.

Figures 5, 6:
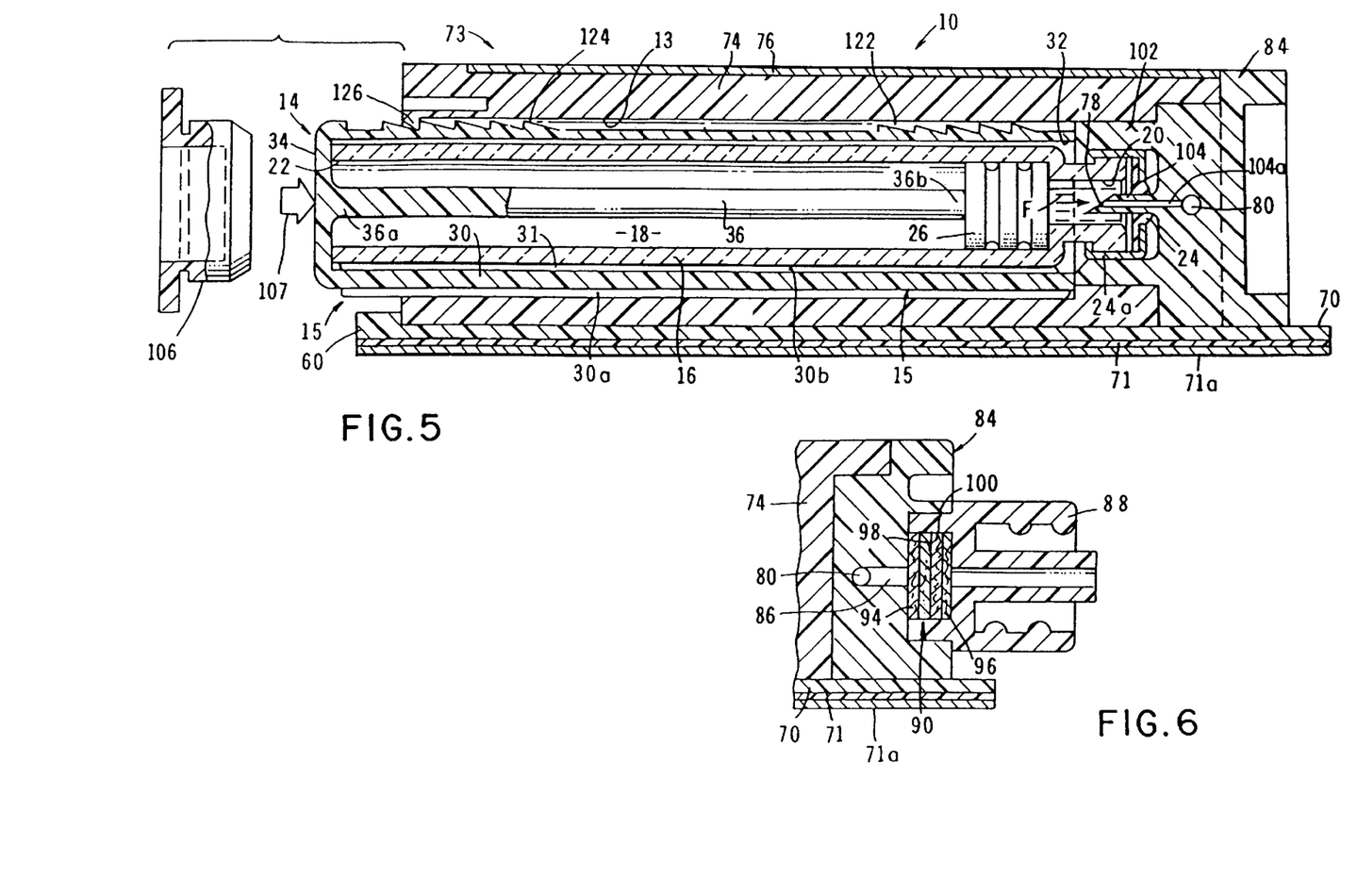
FIG. 5 is a cross-sectional view taken along lines 5—5 of FIG. 2.
FIG. 6 is a cross-sectional view taken along lines 6—6 of FIG. 2.

Passageways 78 and 80 are formed within a housing 84 which is connected to cover member 73, while passageway 81 is formed within upraised portion 68 of base member 70. Housing 84 comprises a part of the cover subassembly of the invention and includes an outlet passageway 86 which communicates with a luer assembly 88 via flow control means generally designated by the numeral 90 (FIGS. 2 and 3). As best seen in FIG. 6, the flow control means here comprises an assemblage make up of four disc-like wafers. Wafers 94 and 96 of the assemblage comprise porous glass distribution frits while intermediate wafers 98 and 100 comprise a filter member and a rate control member respectively.

While filter member 98 can be constructed from a wide variety of materials, a material comprising polysulfone sold by Gelman Sciences under the name and style of SUPOR has proven satisfactory. Rate control member 100 is preferably constructed from a porous material such as polycarbonate material having extremely small flow apertures ablatively drilled by an excimer laser ablation process. Both the orifice size and unit distribution can be closely controlled by this process. However, a number of other materials can also be used to construct this permeable member, including metals, ceramics, cermet, plastics and glass. The rate control member can be specifically tailored to accommodate very specific delivery regimens including very low flow and intermediate flow conditions.

As best seen in FIGS. 2 and 5, housing 84 includes a generally cylindrically shaped hollow hub-like portion 102 which extends into receiving channel 13 when the housing 84 is mated with cover member 74. Formed within hub-like portion 102 is a hollow piercing cannula 104 the purpose of which will presently be described. As indicated in FIG. 2, the internal bore 104a of hollow cannula 104 comprises the previously identified fluid passageway 78, which is in fluid communication with flow passageway 80 of housing 84.

In using the apparatus of the invention, with the fill assembly in the filled configuration shown in FIG. 8, the cover subassembly is first removed from the container subassembly by pulling on pull-tab 42a. This will cause the spiral portion 42 of the cover subassembly to tear away from the container subassembly so that it can be separated from the forwardly disposed portion 52. Once the spiral wound portion 42 is removed, cylindrical portion 52 can also be removed and discarded. Removal of the cover subassembly exposes the forward portion of the container subassembly and septum 24 readies the adapter subassembly for interconnection with the fluid delivery assembly.

Prior to mating the adapter subassembly with the fluid delivery assembly, closure plug 106 of the cover subassembly must be removed in the manner illustrated in FIG. 1. This done, the fill assembly can be telescopically inserted into receiving chamber 13 and pushed forwardly in the direction indicated by the arrow 107 in FIG. 5. A force exerted in the direction of the arrow will cause the adapter subassembly to move to the right as viewed in FIG. 5 and will cause the piercing cannula 104 to pierce septum 24. Once a fluid flow path between fluid chamber 18 of the container subassembly 16 and the fluid reservoir 82 of the fluid delivery assembly is thus created, a continued movement of the adapter subassembly will cause pusher rod 36 to move plunger 26 forwardly of chamber 18 to a position shown in FIG. 5. As plunger 26 is moved forwardly of chamber 18, the fluid "F" contained within the chamber will flow through open end 20, into passageway 104a of the piercing cannula, passageway 80 of housing 84 and then into fluid reservoir 82 via passageway 81. As the fluid under pressure flows into reservoir 82, barrier member 83 will be distended outwardly in the manner shown in FIG. 4 and will uniformly deform the conformable ullage 77 and at the same time distend the distendable membrane 66 until it reaches the position shown in FIG. 4 where it engages inner wall 74a of cover member 74. Gases contained in the volume between wall 74a and the distendable membrane 66 will be vented to atmosphere via vent passageway "V" (FIG. 3). Ring 72, which is in clamping engagement with upstanding portion 68 of base 70 functions to capture and seal the distendable membrane against portion 68. In a similar manner, the periphery of the barrier member 83 is sealably affixed to the upstanding portion 68a of base 70 as by adhesive or thermal bonding, so as to prevent leakage of fluid around the perimeter of the member.

It is to be understood that distendable membrane 66 can comprise a single film layer or can comprise a laminate construction made up of a number of cooperating layers. In this regard, reference should be made to columns 10 and 11 of U.S. Pat. No. 5,411,480 which patent is incorporated herein by reference, wherein the various materials that can be used to construct membrane 66 are discussed in detail. Reference should also be made to columns 11 and 12 of this patent for the various materials that can be used in the construction of the cover and base subassemblies of the fluid delivery apparatus of the present invention. Reference to FIG. 39 of the patent will show a distendable membrane of a laminate construction that can be used in the construction of the fluid delivery device of the present invention (see also columns 17 and 18 of U.S. Pat. No. 5,411,480).

Referring particularly to FIG. 1, it is to be noted that inlet means shown here as an inlet 111 formed in base 70 is provided to enable the introduction of gel which forms the conformable ullage of this form of the invention. Inlet 111 communicates with a fluid passageway 112 which, in turn, communicates with the volume defined between the under surface 66a of membrane 66 and the upper surface 83a of barrier member 83. Inlet 111 is sealably closed by a bonded plug 114.

With the construction described in the preceding paragraphs and as shown in FIGS. 3 and 4, the conformable mass 77, which comprises the ullage defining means of the invention is disposed within a chamber defined by the upper surface 68a of base member 68 and the inner surface or wall 74a of cover 74. Ullage 77 is, as shown in the drawings, in direct engagement with distendable membrane 66 which, after being distended, will tend to return to its less distended configuration. It is to be noted that the shape of the conformable ullage will continuously vary as the distendable membrane distends outwardly from the base during reservoir filling and then tends to return to its less distended configuration during fluid delivery.

While the conformable ullage, or mass 77 is here constructed from a flowable gel, the conformable ullage can also be constructed from a number of materials such as various types of foams, fluids and soft elastomers. In some instances, the conformable ullage may comprise an integral conforming mass. In other instances, such as when a gel or fluid is used as the ullage medium, an encapsulation barrier member such as member 83 must be used to encapsulate the gel or fluid and to provide an appropriate interface to the fluid contained in the reservoir.

Once reservoir 82 is filled with fluid from the container subassembly of the fill assembly, the fluid will remain in the reservoir until such time as the luer cap 89 is removed from luer assembly 88 so as to open the outlet flow path of the fluid delivery assembly. Once the outlet flow path of the assembly is opened, distendable membrane 66 will tend to return to its less distended configuration and will act upon the conformable ullage 77 and the barrier member 83 in a manner to cause fluid to flow from reservoir 82 outwardly through flow passageways 81 and 86 and then into the outlet port 120 of the device via the flow control means 90.

Referring once again to FIGS. 5 and 7, it is to be noted that hollow housing 30 includes locking means for locking the housing within receiving chamber 13 of cover 74 after the fill subassembly has been mated with the fluid delivery device. These locking means are here provided in the form of a series of forwardly and rearwardly disposed locking teeth 122 and 124 respectively. As indicated in FIG. 5, these locking teeth and constructed so that they will slide under a flexible locking tab 126, which is provided proximate the entrance of receiving chamber 13, as the adapter subassembly is urged inwardly of receiving chamber 13. However, once the adapter subassembly has reached the fully inserted position shown in FIG. 5 wherein the fluid is transferred to reservoir 82, locking tab 126 will effectively prevent removal of housing 30 of the adapter subassembly from passageway 13. With this novel construction, once reservoir 82 has been filled with the fluid contained in the container subassembly, the adapter subassembly cannot be removed from the fluid delivery device and, therefore, cannot be reused thereby preventing system adulteration.

Also forming an important aspect of the present invention is the provision of viewing means for viewing at any time the volume of fluid contained within chamber 18 of the fluid container subassembly 14. In the form of the invention shown in the drawings, this viewing means takes the form of an elongated viewing window 130 which is provided in housing 30 (FIG. 7). As indicated in FIG. 7, the body portion 16 of the container subassembly is provided with a plurality of longitudinally spaced-apart index lines, or marks 132, which can be viewed through window 130 as the container subassembly is urged forwardly of housing 30 in the manner previously described. Index lines 132 provide reference points for observing the volume of fluid remaining within the container subassembly. A protuberance 30a formed on housing 30 in cooperation with channel 30b (FIG. 5) functions to provide polarized orientation of the subassembly.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A fluid delivery apparatus comprising:
   (a) a fluid delivery assembly having an outlet for delivering fluid from the apparatus, said fluid delivery assembly including:

(i) a base;
(ii) means defining a conformable ullage overlaying said base for forming in conjunction therewith a reservoir having an outlet in communication with said outlet of said fluid delivery assembly;
(iii) a cover assembly connected to said base, one of said cover assembly and said base having a receiving chamber interconnected with said reservoir; and
(iv) a stored energy means for exerting forces on said means defining a conformable ullage, said stored energy means comprising at least one distendable membrane superimposed over said means defining a conformable ullage, said membrane being distendable by forces imparted thereon by said means defining a conformable ullage in response to fluids introduced into said reservoir, said forces establishing internal stresses within said distendable membrane, said stresses tending to return said distendable membrane toward a less distended configuration, said distendable membrane being generally conformable to the shape of said means defining a conformable ullage as said membrane is being distended thereby and also being generally conformable to the shape of said means defining a conformable ullage as said distendable membrane tends to return to said less distended configuration; and
(b) a fill assembly interconnected with said fluid delivery assembly for filling said reservoir.

2. An apparatus as defined in claim 1 in which said fill assembly comprises:
(a) a container assembly including:
(i) a container having a fluid chamber;
(ii) means associated with said fluid chamber for urging fluid to flow from said fluid chamber toward said reservoir;
(b) an adapter assembly receivable within said receiving chamber, said adapter assembly comprising a hollow housing having a first open end for telescopically receiving a part of said container of said container assembly and including a second end.

3. An apparatus as defined in claim 2 in which said container assembly further includes closure means for closing said container, said container means comprising a pierceable septum connected to said container.

4. An apparatus as defined in claim 3 in which said cover assembly includes piercing cannula disposed within said receiving chamber, said piercing cannula being in communication with said reservoir.

5. An apparatus as defined in claim 4 in which said hollow housing of said adapter assembly includes locking means for locking said hollow housing to said fluid delivery assembly.

6. An apparatus as defined in claim 4 in which said fluid delivery assembly further comprises a barrier member disposed between said base and said means defining a conformable ullage.

7. An apparatus as defined in claim 6 in which said means defining a conformable ullage comprises a conformable mass.

8. An apparatus as defined in claim 6 in which said means defining a conformable ullage comprises a gel.

9. An apparatus as defined in claim 8 in which said gel is encapsulated between said barrier member and said distendable membrane.

10. An apparatus as defined in claim 8 further including means for introducing said gel between said barrier member and said distendable membrane.

11. A fluid delivery apparatus comprising:
(a) a fluid delivery assembly having an outlet for delivering fluid from the apparatus, said fluid delivery assembly including:
(i) a base;
(ii) means defining a conformable ullage of varying shape overlaying said base for forming in conjunction therewith a reservoir having an outlet;
(iii) a barrier member disposed between said base and said means defining a conformable ullage;
(iv) a cover assembly connected to said base, one of said cover assembly and said base having a receiving chamber interconnected with said first end of said fluid passageway formed on said base;
(v) a stored energy means for exerting forces on said means defining a conformable ullage, said stored energy means comprising at least one distendable membrane superimposed over said means defining a conformable ullage, said membrane being distendable by forces imparted thereon by said means defining a conformable ullage in response to fluids introduced into said reservoir, said forces establishing internal stresses within said distenable membrane toward a less distended configuration; and
(b) a fill assembly interconnected with said fluid delivery assembly.

12. An apparatus as defined in claim 11 in which said fill assembly comprises:
(a) a container assembly including:
(i) a container having a body portion, a fluid chamber, and first and second open ends;
(ii) closure means for sealably closing said first end of said container; and
(iii) means associated with said container for urging fluid therefrom; and
(b) an adapter assembly receivable within said receiving chamber, said adapter assembly comprising a hollow housing having a first open end for telescopically receiving a part of said body portion of said container assembly and including a second end.

13. An apparatus as defined in claim 12 in which said means for urging fluid flow from said container comprises a plunger telescopically movable within said container and in which said hollow housing further includes pusher means for engagement with said plunger of said container assembly to move said plunger within said container.

14. An apparatus as defined in claim 12 in which said fill assembly further includes a container cover assembly having a container cover provided with a first open end for telescopically receiving a part of said body portion of said container of said container assembly and a second end, said container cover being removable from said container to expose said closure means.

15. A fluid delivery apparatus comprising:
(a) a fluid delivery assembly having an outlet for delivering fluid from the apparatus, said fluid delivery assembly including:
(i) a base having an upper surface, a lower surface, and a fluid passageway formed therein, said fluid passageway being in communication with said outlet of the apparatus;
(ii) means defining a conformable ullage overlaying said base for forming in conjunction therewith a reservoir having a fluid port in communication with said passageway formed in said base;

(iii) a barrier member disposed between said upper surface of said base and said means defining a conformable ullage;
(iv) a cover assembly connected to said base, said cover assembly including a cover member and a housing connected to said cover member and comprising:
   a. a wall defining an internal cavity within said cover member;
   b. a receiving chamber provided in said cover member and spaced apart from said cavity;
   c. a hollow cannula connected to said housing and extending into said receiving chamber; and
   d. an inlet passageway formed in said housing for interconnecting said hollow cannula with said fluid passageway formed in said base;
(v) a stored energy means for exerting forces on said means defining a conformable ullage, said stored energy means comprising at least one distendable membrane superimposed over said means defining a conformable ullage, said membrane being distendable by forces imparted thereon by said means defining a conformable ullage in response to fluids introduced into said reservoir, said forces establishing internal stresses within said distendable membrane, said stresses tending to return said distendable membrane toward a less distended configuration; and (b) a fill assembly interconnected with said fluid delivery assembly for filling said reservoir thereof via said inlet passageway of said cover assembly, said fill assembly comprising:
(i) a container assembly including:
   a. a container having a body portion, a fluid chamber, and first and second open ends;
   b. closure means for sealably closing said first end of said container said closure means being pierceable by said hollow cannula; and
   c. means operably associated with said container to cause fluid within said fluid chamber to flow into said hollow cannula; and
(ii) an adapter assembly receivable within said chamber of said cover assembly, said adapter assembly comprising a hollow housing having a first open end for telescopically receiving a part of said body portion of said container of said container assembly and including a second end.

\* \* \* \* \*